United States Patent [19]

Gruber et al.

[11] Patent Number: 4,493,883
[45] Date of Patent: Jan. 15, 1985

[54] ELECTROPHOTOGRAPHIC TONER COMPOSITIONS CONTAINING NOVEL IMIDE CHARGE CONTROL ADDITIVES

[75] Inventors: Robert J. Gruber, Rochester, N.Y.; Doretta Agostine, Jenkintown, Pa.; Paul C. Julien, West Webster; Raymond A. Yourd, III, Rochester, both of N.Y.

[73] Assignee: Xerox Corporation, Stamford, Conn.

[21] Appl. No.: 581,926

[22] Filed: Feb. 21, 1984

[51] Int. Cl.³ .............................................. G03G 9/08
[52] U.S. Cl. ..................................... 430/110; 430/120
[58] Field of Search ................................ 430/110, 120

[56] References Cited

U.S. PATENT DOCUMENTS

| | | | |
|---|---|---|---|
| 2,271,122 | 1/1942 | Harman | 260/784 |
| 3,151,160 | 9/1964 | Spivack | 260/570.5 |
| 3,894,043 | 7/1975 | Moser et al. | 260/326.5 S |
| 4,248,719 | 2/1981 | Chafetz et al. | 252/34 |
| 4,298,672 | 11/1981 | Lu | 430/108 |
| 4,338,390 | 7/1982 | Lu | 430/106 |
| 4,415,646 | 11/1982 | Gruber et al. | 430/110 |

Primary Examiner—John D. Welsh
Attorney, Agent, or Firm—E. O. Palazzo

[57] ABSTRACT

Disclosed are positively charged toner compositions comprised of resin particles, pigment particles, and imide charge enhancing additives of the formula:

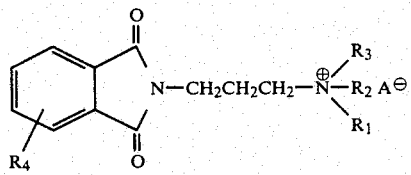

wherein $R_1$, $R_2$, and $R_3$, are alkyl groups containing from 1 carbon atom to about 25 carbon atoms, $R_4$ is selected from the group consisting of hydrogen, nitro, halogen, amino, and alkyl and A is an anion.

24 Claims, No Drawings

ELECTROPHOTOGRAPHIC TONER COMPOSITIONS CONTAINING NOVEL IMIDE CHARGE CONTROL ADDITIVES

BACKGROUND OF THE INVENTION

This invention is generally directed to toner compositions, and more specifically, the present invention is directed to developer compositions and toner compositions, including magnetic toner compositions, containing certain charge enhancing additives, which additives impart a positive charge to the toner resin particles. Developer compositions containing the imide charge enhancing additives of the present invention are useful for causing the development of electrostatic latent images, including color images. More specifically positively charged toner compositions containing the imide additives are particularly useful in electrostatographic imaging systems having incorporated therein a Viton coated fuser roll, since these imides do not react substantially with Viton, causing undesirable decomposition thereof, which adversely affects image quality.

Developer compositions containing charge enhancing additives, especially additives which impart a positive charge to the toner resin are well-known. Thus for example there is described, in U.S. Pat. No. 3,893,935 the use of certain quaternary ammonium salts as charge control agents for electrostatic toner compositions. In accordance with the disclosure of this patent, certain quaternary ammonium salts when incorporated into a toner material provided a composition which exhibited relatively high uniform stable net toner charge when mixed with a suitable carrier vehicle; which toner also exhibited a minimum amount of toner throw off.

There is also described in U.S. Pat. No. 2,986,521, reversal developer compositions comprised of toner resin particles coated with finely divided colloidal silica. According to the disclosure of this patent the development of electrostatic latent images on negatively charged surfaces is accomplished by applying a developer composition having a positively charged triboelectric relationship with respect to the colloidal silica.

Also there is disclosed in U.S. Pat. No. 4,338,390 developer and toner compositions having incorporated therein as charge enhancing additives organic sulfate and sulfonate compositions.

Other patents disclosing charge control additives include U.S. Pat. Nos. 3,944,493, 4,007,293, 4,079,014, and 4,394,430.

Further there is disclosed in U.S. Pat. No. 4,298,672 positively charged toner compositions containing resin particles, and pigment particles, and as a charge enhancing additive alkyl pyridinium compounds and their hydrates of the formula as detailed in Column 3, beginning at line 14. Examples of alkyl pyridinium compounds disclosed include cetyl pyridinium chloride. While the developer compositions disclosed in the 672 patent are sufficient for their intended purposes it appears that the alkyl pyridinium compounds involved react with the polymer contained on Viton fuser rolls causing decomposition thereof. Also several of the other charge control agents disclosed in the prior art interact with certain fuser rolls, such as Viton fuser rolls, used in electrostatographic systems. This interaction causes the fuser to be adversely affected, resulting in deterioration of the image quality. For example, Viton fuser rolls discolor and turn black, develop multiple surface cracks and harden, when certain charge control additive compounds are contained in the toner mixture.

One Viton fuser roll selected for use in electrostatographic copying machines, is comprised of a soft roll fabricated from lead oxide, and duPont Viton E-430 resin, a vinylidene fluoride hexafluoropropylene copolymer. This roll contains approximately 15 parts of lead oxide, and 100 parts of Viton E-430, which mixture is blended and cured on the roll substrate at elevated temperatures. Apparently the function of the lead oxide is to generate unsaturation by dehydrofluorination for crosslinking, and to provide release mechanisms for the toner composition. Excellent image quality has been obtained with Viton fuser rolls, however, in some instances there results a toner fuser compatibility problem when charge control agents are part of the toner mixture. For example, it appears that certain specific charge control additivies, such as quaternary ammonium compounds, and alkyl pyridinium compounds, including cetyl pyridinium chloride, react with the Viton of the Viton fuser roll. For example, cetyl pyridinium chloride when part of the toner mixture appears to be catalytically decomposed by the lead oxide contained in the fuser roll, resulting in a highly unsaturated compound, which polymerizes and condenses with the unsaturated Viton E-430 material. In view of this, the Viton fuser roll turns black, develops multiple surface cracks, and the surface thereof hardens, thereby resulting in image quality deterioration.

Toner compositions containing many of the above described charge enhancing additives are useful for causing the development of images formed on layered photoresponsive imaging devices comprised of generating layers and transport layers. These devices usually are charged negatively, rather than positively as is the situtation with selenium photoreceptors, thereby requiring a toner composition that is positively charged in order that the toner particles may be suitable attracted to the electrostatic latent image contained on the photoreceptor surface. In view of this efforts have been devoted to obtaining developer compositions containing toner resins which are positively charged. Thus while many charge control additives are known, there continues to be a need for new additives. Spesifically there continues to be a need for additives which will not interact with Viton type fuser rolls. Additionally, there continues to be a need for charge control additives which are thermally stable at high temperatures. Moreover, there continues to be a need for positively charged toner and developer compositions which are humidity insensitive since it is known that moisture contained in the atmosphere, or moisture from other sources, can adversely effect the electrical properties of the toner compositions involved.

Also there continues to be a need for new charge ehancing additives, particularly those additives which can be economically prepared. Additionally there is a need for additives which in addition to being thermally stable, are substainally nontoxic. Further there is a need for charge enhancing additives which can be easily and permanently dispersed in toner resin particles. Moreover there is a need for toner compositions which contain positively charged resin particles, and wherein the resulting toner compositions have desirable toner admix charging.

SUMMARY OF THE INVENTION

It is an object of the present invention to provide toner and developer compositions containing imide charge enhancing additives, which overcome the above-noted disadvantages.

In another object of the present invention there is provided positively charged toner compositions which are useful for causing the development of electrostatic latent images, including color images.

In yet another object of the present invention there is provided positively charged toner compositions containing as charge enhancing additives imide compositions.

A further object of the present invention is to provide charge enhancing additives which are thermally stable at high temperatures.

Another object of the present invention resides in the provision of novel tetrafluoroborate charge enhancing additives which do not interact and/or attack Viton rubber selected for use in imaging systems containing certain fusing roll systems.

In another object of the present invention there is provided a developer composition containing positively charged toner particles, carrier particles and imide charge enhancing additives.

In yet a further object of the present invention there are provided positively charged toner compositions which are water insensitive and have desirable admix properties.

In a further object of the present invention there are provided magnetic toner compositions, and colored toner compositions containing positively charged toner particles, carrier particles, and imide charge enhancing additives.

These and other objects of the present invention are accomplished by providing developer compositions, and toner compositions, wherein the dry electrostatic toner compositions are comprised of resin particles, pigment particles, and imide charge enhancing additives of the following formula:

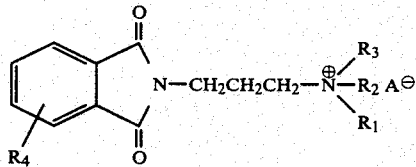

where $R_1$, $R_2$, and $R_3$, are alkyl groups containing from about 1 carbon atom to about 25 carbon atoms, $R_4$ is hydrogen, nitro, halogen, amino, or an alkyl group, and A is a suitable anion. Preferred imide charge enhancing additives include those wherein the alkyl groups contain from about 1 carbon atom to about 10 carbon atoms. Also useful as charge enhancing additives are those imide compositions wherein the propylene group in the above formula is replaced with other alkylene groups such as those containing from 1 to 2 carbon atoms, and 4 to 10 carbon atoms, including methylene, ethylene, butylene, pentylene, and the like.

Illustrative examples of alkyl groups include methyl, ethyl, propyl, butyl, pentyl, hexyl, octyl, nonyl, decyl, cetyl, stearyl, eicosyl, pentadecyl and the like, with methyl being preferred.

Illustrative examples of the anion group include halogens such as, chlorine, bromide, iodide, and fluoride, sulfate, tosylate, sulfonate, tetrafluoroborate, and the like, with sulfonate, and tetrafluoroborate, being preferred. The tetrafluoroborates are beleived to be novel compositions of matter.

Examples of charge enhancing additives included with the scope of the present invention, and embraced by the above formula are (3-phthalimidopropyl)trimethylammonium methylsulfate, (3-succinimdopropyl)-trimethylammonium methylsulfate, (3-[n-hexadecylsuccinimido]propyl)trimethylammonium methylsulfate, (3-phthalimidopropyl)dimethylcetylammonium bromide, (3-succinimidopropyl)dimethylcetylammonium bromide, (3-phthalimidopropyl)trimethylammonium tetrafluoroborate, (3-phthalimidopropyl)dimethylcetylammonium tetrafluoroborate, (3-phthalimidopropyl)dimethylethyl ammoniumtosylate, (3-succinimidopropyl)dimethylethylammonium tosylate, (3-succinimidopropyl)trimethylammonium tetrafluoroborate, and the like.

The imide charge enhancing additives of the present invention can be prepared for example, by refluxing the appropriate anhydride with a dialkylaminoalkylene amine such as dialkylaminopropylamine, in a suitable aromatic solvent, such as xylene or toluene, which solvent assists in removing any water that is formed during the reaction, this removal being accomplished by for example azeotropic distillation, the reaction generally occuring in the presence of a catalyst such as a trialkylamine. More specifically, there is reacted an excess of a dialkylaminopropylamine, such as dimethylaminopropylamine, with an effective amount, for example from about 0.01 to 0.1 moles, of a trialkylamine catalyst, such as triethylamine. These reactants are dissolved in a suitable aromatic organic solvent, such as xylene, and subsequently, there is added to the reaction mixture an appropriate anhydride, such as phthalic anhydride, succinic anhydride, hexadecyl succinic anhydride, and the like, followed by heating the mixture to a sufficient temperature so as to cause the anhydride to dissolve, this temperature being, for example, from about 90° C. to about 120° C., and preferably from about 110° C. to about 115° C. Thereafter an azeotropic distillation is effected by heating the reaction mixture to full reflux, usually from about 140° C. to about 145° C., when xylene is used as the solvent, which reflux is continued until all the water has been removed from the reaction mixture. Any excess solvent, such as xylene and excess amines are then removed from the reaction mixture, by known techniques, such as the use of a rotary evaporator. There results the desired crude imide, which is in the form of an oil that crystallizes on standing. These imides which may be further purified by vacuum distillation, were identified by various techniques, including standard elemental analysis, infrared spectroscopy and melting point determinations.

The resulting imide products can then be quaternized by known processes, wherein the charge enhancing additives of the present invention result. More specifically, with the exception of the tetrafluoroborates, the quaternization can be accomplished by reacting the above prepared imides with a variety of alkylating agents, such as alkyl halides, of the formula

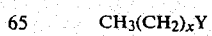

wherein y is a halogen such as chlorine, or bromine, and x is a number of from about 10 to about 18, however x can also be zero, or a number of from about 1 to about 9; alkyl toluene sulfonates, of the formula

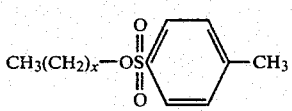

wherein x is a number of from 1 to about 20, and preferably x is a number of from 1 to about 16, dimethylsulfates, and the like. The corresponding novel tetrafluoroborate salts are prepared for example by dissolving the above prepared methyl sulfate imide quaternary salts in an aqueous solution, followed by the addition of a salt of a tetrafluoroborate, such as sodium tetrafluoroborate. There results a tetrafluoroborate precipitate. The resulting product can then be obtained by filtration from the reaction mixture.

More specifically, the tetrafluoroborate salt is prepared by first forming a quaternary salt by dissolving for example N-[3-dialkylaminopropyl]phthalimide in a solvent such as acetone. The resulting solution is then immersed in an ice bath for the purpose of lowering the temperature thereof to below about 10° C. and subsequently there is slowly added to the reaction mixture a dialkylsulfate such as dimethylsulfate which has been dissolved in a suitable solvent like acetone. Shortly thereafter there results a white precipitate product of 3-phthalimidopropyltrimethylammonium alkylsulfate isolated by filtration. The product was identified by elemental analysis, melting point data, and infrared spectroscopy.

The above prepared alkylsulfate product is then dissolved for example in water and there is added thereto an alkalitetrafluoroborate such as sodium tetrafluoroborate which has been dissolved in for example water. The sodium tetrafluoroborate solution is added slowly to the reaction mixture and shortly thereafter there result a white product precipitate of for example phthalimidopropyltrimethylammonium tetrafluoroborate, which is filtered from the mixture and subsequently identified by melting point data, elemental analysis and infrared spectroscopy.

Illustrative examples of suitable toner resins selected for the toner and developer compositions of the present invention include polyimides, epoxies, polyurethanes, vinyl resins and polymeric esterification products of a dicarboxylic acid and a diol comprising a diphenol. Any suitable vinyl resin may be selected for the toner resins of the present application including homopolymers or copolymers of two or more vinyl monomers. Typical of such vinyl monomeric units include: styrene, p-chlorostyrene vinyl napthalene unsaturated monoolefins such as ethylene, propylene, butylene, isobutylene and the like; vinyl halides such as vinyl chloride, vinyl bromide, vinyl fluoride, vinyl acetate, vinyl propionate, vinyl benzoate, vinyl butyrate and the like; vinyl esters such as esters of monocarboxylic acids including methyl acrylate, ethyl acrylate, n-butylacrylate, isobutyl acrylate, dodecyl acrylate, n-octyl acrylate, 2-chloroethyl acrylate, phenyl acrylate, methylalpha-chloroacrylate, methyl methacrylate, ethyl methacrylate, butyl methacrylate, and the like; acrylonitrile, methacrylonitrile, acrylimide, vinyl ethers, such as vinyl methyl ether, vinyl isobutyl ether, vinyl ethyl ether, and the like; vinyl ketones such as vinyl methyl ketone, vinyl hexyl ketone, methyl isopropenyl ketone and the like; vinylidene halides such as vinylidene chloride, vinylidene chlorofluoride and the like; and N-vinyl indole, N-vinyl pyrrolidene and the like; styrene butadiene copolymers, and mixtures thereof.

As one preferred toner resin there can be selected the esterification products of a dicarboxylic acid and a diol comprising a diphenol. These materials are illustrated in U.S. Pat. No. 3,590,000, the disclosure of which is totally incorporated herein by reference. Other preferred toner resins include styrene/methacrylate copolymers, and styrene/butadiene copolymers, polyester resins obtained from the reaction of bis-phenol A and propylene oxide, followed by the reaction of the resulting product with fumaric acid, and branched polyester resins resulting from the reaction of dimethylterephthalate, i,3-butanediol, 1,2-propanediol, and pentaerthriol.

The resin particles are present in a sufficient, but effective amount an amount, thus when 5 percent by weight of the novel imide composition and 10 percent by weight of pigment, or colorant such as carbon black is contained therein, about 85 percent by weight of resin material is selected. Generally from about 0.1 weight percent to about 10 weight percent and preferably from about 1 weight percent to about 5 weight percent, of the imide is selected for mixing with the toner particles, however the charge enhancing additive of the present invention can be used in various other amounts providing the objectives of the present invention are accomplished. The imide charge enhancing additive of the present invention can be blended into the toner composition, or coated on the pigment particles, such as carbon black, which are used as the colorants in the developer composition. When used as a coating, the charge enhancing additive of the present invention is present in an amount of from about 0.1 weight percent to about 5 weight percent and preferably in an amount of from about 0.3 weight percent to about 1 weight percent.

Numerous well known suitable pigments or dyes can be selected as the colorant for the toner particles including for example, carbon black nigrosine dye, aniline blue, magnetites and mixtures thereof. The pigment, which is preferably carbon black, should be present in a sufficient amount to render the toner composition highly colored in order that it will cause the formation of a clearly visible image on a suitable recording member. Generally, the pigment particles are present in amounts of from about 3 percent by weight to about 20 percent by weight, based on the total weight of the toner composition, however, lesser or greater amounts of pigment particles can be selected providing the objectives of the present invention are achieved.

When the pigment particles are comprised of magnetites, which are a mixture of iron oxides ($FeO.Fe_2O_3$) including those commercially available as Mapico Black, these pigments are present in the toner composition in an amount of from about 10 percent by weight to about 70 percent by weight, and preferably in an amount of from about 20 percent by weight to about 50 percent by weight. Toner compositions containing such pigments are referred to as magnetic toner compositions.

Also embraced within the scope of the present invention are colored toner compositions containing toner resin particles, carrier particles, the imide charge enhancing additives illustrated herein, and as pigments or colorants, magenta, cyan, and/or yellow particles, as well as mixtures thereof. More specifically, with regard to the production of color images utilizing a developer composition containing the charge enhancing additives of the present invention, illustrative examples of magenta materials that may be selected as pigments, include for example, 2,9-dimethyl-substituted quinacridone and anthraquinone dye indentified in the color index as CI 60710, CI Dispersed Red 15, a diazo dye identified in the color index as CI 26050, CI Solvent Red 19, and the like. Illustrative examples of cyan materials that may be used as pigments include copper tetra4(octadecyl sulfonamido) phthalocyanine, X-copper phthalocyanine pigment listed in the color index as CI 74160, CI Pigment Blue, and Anthrathrene Blue, identified in the color index as CI 69810, Special Blue X-2137, and the like; while illustrative examples of yellow pigments that may be selected include diarylide yellow 3,3-dichlorobenzidene acetoacetanilides, a monoazo pigment identified in the color index as CI 12700, CI Solvent Yellow 16, a nitrophenyl amine sulfonimide identified in the color index as Foron yellow SE/GLN, CI dispersed yellow 33, 2,5-dimethoxy-4-sulfonanilide phenylazo-4'-chloro-2,5-dimethoxy aceto-acetanilide, permanent yellow FGL, and the like.

These pigments namely, cyan, magenta, and yellow when used with the charge enhancing additives of the present invention are generally present in the toner composition an amount of from about 2 weight percent to about 15 weight percent based on the weight of the toner resin particles.

Illustrative examples of carrier particles that can be selected for mixing with the toner particles of the present invention include those particles that are capable of triboelectrically obtaining a charge of opposite polarity to that of the toner particles. Accordingly, the carrier particles of the present invention are selected so as to be of a negative polarity in order that the toner particles which are positively charged will adhere to and surround the carrier particles. Illustrative examples of such carrier particles include granular zircon, granular silicon, methyl methacrylate, glass, steel, nickel, iron ferrites, silicon dioxide, and the like. Additionally, there can be selected as carrier particles nickel berry carriers as disclosed in U.S. Pat. No. 3,847,604, which carriers are comprised of nodular carrier beads of nickel, characterized by surfaces of reoccurring recesses and protrusions thereby providing particles with a relatively large external area.

The selected carrier particles can be used with or without a coating, the coating generally containing fluoropolymers, such as polyvinylidenefluoride resins, terpolymers of styrene, methylmethacrylate, and a silane, such as triethoxy silane, tetrafluoroethylenes, other known coatings and the like.

The diameter of the carrier particles can vary generally the diameter is from about 50 microns to about 1,000 microns, thus allowing these particles to possess sufficient density and inertia to avoid adherance to the electrostatic images during the development process. The carrier particles can be mixed with the toner particles in various suitable combinations, however, best results are obtained when about 1 part per toner to about 10 parts to about 200 parts by weight of carrier are mixed.

The toner composition of the present invention can be prepared by a number of known methods, including melt blending the toner resin particles, pigment particles or colorants, and the imide charge enhancing additive of the present invention, followed by mechanical attrition. Other methods include those well known in the art such as spray drying, melt dispersion, dispersion polymerization, and suspension polymerization. In one dispersion polymerization method, a solvent dispersion of the resin particles, the pigment particles, and the imide charge enhancing additive are spray dried under controlled conditions to result in the desired product. Toner compositions prepared in this manner result in a positively charged toner composition in relation to the carrier materials selected, and these materials exhibit the improved properties as mentioned hereinbefore.

The toner and developer compositions of the present invention may be selected for use in developing images in electrostatographic imaging systems, containing therein conventional photoreceptors providing that they are capable of being charged negatively. This usually occurs with organic photoreceptors illustrative examples of which include layered photoresponsive devices comprised of transport layers and photogenerating layers, reference U.S. Pat. No. 4,265,990, the disclosure of which is totally incorporated herein by reference, and other similar layered photoresponsive devices. Examples of generating layers include trigonal selenium, metal phthalocyanines, metal free phthalocyanines and vanadyl phthalocyanines, while examples of charge transport layers include the diamines as disclosed in U.S. Pat. No. '990. Other photoresponsive devices useful in the present invention include polyvinylcarbazole 4-dimethylaminobenzylidene, benzhydrazide; 2-benzylidene-aminocarbazole, 4-dimethaminobenzylidene, (2-nitro-benzylidene)-p-bromoaniline; 2,4-diphenyl-quinazoline; 1,2,4-triazine; 1,5-diphenyl-3-methyl pyrazoline 2-(4'-dimethyl-amino phenyl)-benzoaxzole; 3-aminocarbazole, polyvinyl carbazole-trinitrofluorenone charge transfer complex; and mixtures thereof.

The following examples are being supplied to further define various species of the present invention, it being noted that these examples are intended to illustrate and not limit the scope of the present invention. Parts and percentages are by weight unless otherwise indicated.

EXAMPLE I

There was prepared (3-phthalimidopropyl)trimethylammonium tetrafluoroborate by dissolving 145 grams, 1.42 moles, of dimethylaminopropylene, and 3.92 grams, 0.039 moles of triethylamine in one liter of xylene, in a two litered three necked round bottom flask equipped with a stirrer, a thermometer, a heating mantle, a Dean-Stark trap, and a reflux condenser. Subsequently 191.3 grams, 1.29 moles of phthalic anhydride was added, and the mixture was refluxed at a temperature of 140 degrees centigrade. Subsequent to refluxing for 24 hours, 24 milliliters of water was collected in the Dean-Stark trap. The xylene and excess amines were then removed from the reaction mixture on a rotary evaporator yielding the crude product N-(dimethylaminopropyl)phthalimide, in a yield of 300 grams. The crude imide separated was a brown syrup which crystallized on standing. This imide product, subsequent to purification by vacuum distillation, was identified by elemental analysis and infrared spectroscopy.

Thereafter the above prepared imide was quaternized by dissolving 300 grams, 1.29 moles of the imide in 1.5 liters of acetone in a five liter, three necked round bottom flask equipped with a stirrer, a thermometer, and a dropping funnel. The resulting solution was chilled to 10 degrees centigrade by immersing the flask in an ice bath. There was then added dropwise to the imide solution contained in the reaction flask, 200 grams, 1.58 moles, of dimethylsulfate dissolved in 500 milliliters of acetone. A white precipitate was immediately formed. The mixture was then stirred for two hours, and subsequently the resulting product was filtered, washed with acetone, and dried, resulting in the charge enhancing additive (3-phthalimidopropyl)trimethylammonium methylsulfate 472.9 grams, 97.8 percent yield, which sulfate had a melting point of 187 degrees centigrade to 188 degrees centigrade. Addtionally elemental analysis for carbon, hydrogen, nitrogen, oxygen, and sulphur were as follows:

Elemental Analysis: Theory: C: 50.27, H: 6.19, N: 7.82, O: 26.78, S; 8.95. Found: C: 50.41, H: 6.32, N: 7.75, S: 8.90.

There was then dissolved in two liters of water contained in a three necked round bottom flask equipped with a stirrer, and a dropping funnel, 425 grams, 1.186 moles, of the above prepared methylsulfate salt. Subsequently 143.21 grams, 1.304 moles, of sodium tetrafluoroborate was dissolved in 700 millliters of water and filtered into the dropping funnel. The sodium tetrafluoroborate solution was added dropwise to the five liter reaction flask and after several minutes a white precipitate formed. The mixture stirred for two hours and the resulting product was filtered, and dried, yielding 352.5 grams, 89.0 percent, of (3-phthalimidopropyl)trimethylammonium tetrafluoroborate, having a melting point of 244 degrees centigrade to 245 degrees centigrade. Additionally elemental analysis for carbon, hydrogen, nitrogen, oxygen, boron and fluoride were as follows:

Elemental Analysis: Theory: C: 50.33, H: 5.73, N: 8.38, O: 9.58, B: 3.24, F: F22.74. Found: C: 50.42, H: 5.83, N: 8.38, B: 3.35, F: 22.53.

Experimental data resulting from thermogravimetric analysis indicates that the temperature at which decomposition of the above tetrafluoroborate product occurs, that is were weight loss of material begins, was 243 degrees centigrade, while the temperature at which decomposition is the highest was 313 degrees centigrade.

EXAMPLE II

There was prepared a toner composition by melt blending at a temperature of 100° C., followed by mechanical attrition, 2 percent by weight of (3-phthalimidopropyl)trimethyl ammonium tetrfluoroborate prepared in accordance with Example I, 6 percent by weight of Regal 330 carbon black, and 92 percent by weight of a styrene butadiene resin, containing 89 percent by weight of styrene, and 11 percent by weight of butadiene, commercially available from Goodyear Chemical Company as Pliolite. The resulting toner was classified in order to remove particles smaller than 5 microns in diameter.

The triboelectric charge on this toner was measured against a Hoeganese steel carrier coated with 0.15 percent by weight of Kynar 301, a polyvinylidene fluoride resin commercially available from Pennwalt Company, at 3 percent toner concentration, such triboelectric measurements being accomplished on a toner charge spectrograph. This instrument dispenses toner particles in proportion to the charge to diameter ratio and with the aid of automated microscopy can generate charge distribution histograms for selected toner size classes. The resulting toner compositions had a positive charge of 1.6 femtocoulombs per micron.

When uncharged toner particles containing 92 percent by weight of the above Pliolite resin, 6 percent by weight of carbon black, and 2 percent by weight of the above phthalimidopropyl)trimethyl ammonium tetrfluoroborate was mixed with a charged developer composition containing 2 percent by weight of phthalimidopropyl)trimethyl ammonium tetrfluoroborate, 6 percent by weight of Regal 330 carbon black, and 92 percent by weight of a Pliolite styrene butadiene resin, containing 89 percent by weight of styrene, and 11 percent by weight of butadiene, the admix charging rate for the uncharged toner composition was less than 15 seconds. Also admix charging experiments evidenced that the uncharged toner particles had fast charging properties when fresh uncharged toner particles were added to the charged developer composition, that is the fresh toner particles became positively charged in less than 15 seconds.

The above experiments were repeated for the purpose of determining the charge admix properties of a toner composition that did not contain the phthalimide tetrafluoroborate charge enhancing additive. There was thus prepared a toner composition, comprised of 94 percent by weight of a styrene butadiene resin, containing 89 percent by weight of styrene, and 11 percent by weight of butadiene, commercially available as Pliolite, and 6 percent by weight of Regal 330 carbon black. This composition had a charge thereon of 0.6 femtocoulombs per micron, and an admix rate greater than 8 minutes. These measurements were again accomplished on a toner charge spectrograph.

The above developer composition was then selected for developing images in a xerographic imaging device, containing a layered photoreceptor comprised of a Mylar substrate, overcoated with a photogenerating layer of trigonal selenium, dispersed in a polyvinyl carbazole binder, and as top layer in contact with the photogenerating layer, charge transport molecules N,N'-diphenyl-N,N'-bis(3-methylphenyl)1,1'-biphenyl-4,4'-diamine, dispersed in a polycarbonate resin commercially available as Makralon, which device was prepared in accordance with the disclosure of U.S. Pat. No. 4,265,990, and there resulted high quality images. The device selected also contained a Viton fuser roll and visual observation after 50,000 imaging cycles indicated that no damage occurred to the Viton fuser roll, that is, the Viton did not turn black, did not crack and the surface did not harden, but rather remained smooth and soft, although very slightly darkened.

When cetyl pyridinium chloride in the same amount, was substituted for the phthalimide tetrafluorborate in the above developer composition, and images were developed with this composition, excellent quality images were initially obtained, however, the Viton fuser roll blackened and appeared to develop surface cracks; and the Viton surface hardened, after about 5,000 imaging cycles. Image quality deteriorated rapidly after about 5,000 imaging cycles, and image resolution was very poor due to the reaction of the cetyl pyridinium chloride with the Viton fuser roll.

Additionally, toner compositions containing the phthalimide tetrafluoroborate charge enhancing additive were humidity insensitive in that the initial tribocharge was only reduced from 1.6 femtocoulombs to 1.3 femtocoulombs, while toner compositions containing the cetyl pyridinium chloride were humidity sensitive in that the charge was significantly reduced from 1.8 femtocoulombs to 1.1 femtocoulombs. These humidity sensitivity measurements were accomplished by the following procedure: The developer compositions involved, one of which contains phthalimide tetrafluoroborate, and one of which contains cetyl pyridinium chloride, was placed in a humidity chamber maintained at a temperature of 80° F. at a relative humidity of 80 percent. These conditions were maintained for 24 hours. The charge on the toner composition and the admix rate were then compared to the results at room temperature at 35 percent relative humidity.

EXAMPLE III

The procedure of Example II was repeated with the exception that the toner composition prepared contained 92 percent by weight of polyester resin particles resulting from the condensation of bis-phenol A, and propylene oxide, followed by reaction of the resulting product with fumaric acid. Other toner compositions were prepared in substantially a similar manner with the exception that there was used as the toner resin particles, a styrene butadiene resin, containing about 90 percent by weight of styrene and 10 percent by weight of butadiene, commercially available from Goodyear Chemical Company; or styrene n-butylmethacrylate resins, containingg 58 percent by weight of styrene and 42 percent by weight of n-butylmethacrylate.

When these toner compositions with the tetrafluoroborate additive were selected for use in the electrostatographic developing system of Example II, substantially similar results were obtained, that is high quality images resulted and the Viton fuser roll did not develop surface cracks, did not turn black or discolor, and the surface thereof did not harden after 35,000 imaging cycles.

A Viton fuser roll test was also accomplished by inserting a strip of Viton approximately ⅛" thick, a length of ¾" and a width of ½", in separate charge enhancing additives contained in a test tube containing 50 percent thereof of the charge enhancing additive to be tested. The test tube was then heated to 200° C. for a period of 24 hours and the Viton fuser strip was removed. After removal and drying, the Viton fuser strip was examined visually for discoloration, surface cracks and a determination was made as to whether the surface thereof hardened by for example, using a durometer, which measures indentation hardness. With the tetrafluoroborate charge enhancing additive as prepared in Example I, no discoloration, or surface cracks were visually observed, and the surface of the Viton did not harden, while with cetyl pyrdinium chloride discoloration, and surface cracks were visuably observable.

EXAMPLE IV

There was prepared (3-phthalimidopropyl)cetyldimethyl ammonium bromide by dissolving 5 grams, 0.022 moles of N-(3-dimethylaminopropyl)phthalimide in 80 milliliters of acetone in a 250 milliliter three necked round bottom flask equipped with a magnetic stirrer, reflux condenser, and a nitrogen blanket. Cetyl bromide, 6.72 grams, 0.022 moles was then added to the flask, followed by heating to reflux. After refluxing for three days the acetone solvent was removed with a rotary evaporator, and there resulted in the form of white crystals the desired product, which was purified by recrystallization in acetone, followed by drying in a vacuo overnight. The product obtained was identified by elemental analysis, and infrared analysis.

EXAMPLE V

There was prepared (3-succinimidopropyl)ethyldimethylammonium tosylate by dissolving 71.9 grams, 0.39 moles of N-(3-dimethylaminopropyl)succinimide in 100 milliliters of acetonitrile contained in a 500 milliliter round bottom flask equipped with a reflux condenser, a magnetic stirrer, heating mantle and a nitrogen blanket. Ethyl-p-toluenesulfonate, 78.1 grams was added to the flask, and the resulting solution was heated under reflux for three days. Subsequent to cooling to room temperature the acetonitrile solvent was removed on a rotary evaporator, and the resulting white crystal product where further purified by recrystallization. The product obtained was identified by elemental analysis, and infrared analysis.

EXAMPLE VI

There was prepared (3-phthalimidopropyl)cetyldimethylammonium tosylate by dissolving 10 grams, 0.054 moles of N-(3-dimethylaminopropyl)succinimide and 21.52 grams, 0.054 moles of cetyl-p-toluenesulfonate in 150 millliters of acetone contained in a 250 round bottom flask equipped with a reflux condenser, a heating mantle, a magnetic stirre, and a nitrogen blanket. The solution was then heated to reflux for three days, and the solvent was removed on a rotary evaporator. There resulted a product white crystals, which was further purified by recrystallization. The product obtained was identified by elemental analysis, and infrared analysis.

Developer compositions were also prepared by repeating the procedure of Example I with the exception that there was used as charge enhancing additives the quaternary ammonium compounds as prepared in Examples IV to VI, and the methylsulfate additive of Example I. When used for developing images in the xerographic imaging device of Example I substantially similar results were obtained.

Other modifications of the present invention may occur to those skilled in the art based upon a reading of the present disclosure and these modifications are intended to be included within the scope of the present invention.

We claim:

1. An improved positively charged toner composition comprised of resin particles, pigment particles, and an imide charge enhancing additive of the following formula:

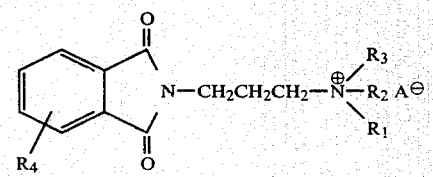

wherein $R_1$, $R_2$, and $R_3$, are alkyl groups of from 1 carbon atom to about 25 carbon atoms, $R_4$ is selected from the group consisting of hydrogen, nitro, halogen, amino and alkyl and A is an anion.

2. A composition in accordance with claim 1 wherein the imide charge enhancing additive is present in an amount of from about 0.1 percent by weigh to about 10 percent by weight.

3. A composition in accordance with claim 1 wherein the imide additive is present in an amount of from about 5 percent by weigh to about 1 percent by weight.

4. A composition in accordance with claim 1 wherein $R_1$, $R_2$, and $R_3$, are alkyl groups of from 1 carbon atom, to about 10 carbon atoms and $R_4$ is hydrogen.

5. A composition in accordance with claim 1 wherein the alkyl groups are methyl.

6. A composition in accordance with claim 1 wherein the anion is chloride, bromide, iodide, fluoride, sulfate, sulfonate, or tetrafluoroborate.

7. A composition in accordance with claim 1 wherein the toner resin particles are polyesters, or styrene based polymers.

8. A composition in accordance with claim 7 wherein the the styrene based polymers are styrene methacrylate, or styrene butadiene.

9. A composition in accordance with claim 1 wherein the resin particles are comprised of a styrene butadiene copolymer, a polyester, or a styrene n-butyl methacrylate copolymer, and the pigment particles are comprised of carbon black.

10. A composition in accordance with claim 1 wherein the resin particles are present in an amount of from 70 percent by weight to about 90 percent by weight, the pigment particles are present in an amount of from about 5 percent by weight to about 20 percent by weight, and the imide charge enhancing additive particles are present in an amount of from 0.1 percent by weight to about 10 percent by weight.

11. A composition in accordance with claim 1 wherein the charge enhancing additive is (3-phthalimidopropyl) trimethylammonium tetrafluoroborate.

12. A composition in accordance with claim 1 wherein the charge enhancing additive is (3-phthalimidopropyl) trimethylammonium methylsulfate.

13. A developer composition comprised of the positively charged toner composition of claim 1, and carrier particles.

14. A developer composition in accordance with claim 13 wherein the carrier particles are comprised of steel, coated with a polymeric resin.

15. A developer composition in accordance with claim 13 wherein the resin particles are selected from a group consisting of styrene methacrylate resins, styrene acrylate resins, styrene butadiene resins or polyester resins.

16. A developer composition in accordance with claim 12 wherein the imide charge enhancing additive is (3-phthalimidopropyl) trimethylammonium methylsulfate.

17. A developer composition in accordance with claim 13 wherein the imide charge enhancing additive is (3-phthalimidopropyl) trimethylammonium tetrafluoroborate.

18. A method of imaging which comprises forming a negative electrostatic latent image on a photoresponsive imaging member, contacting the resulting image with the toner composition of claim 1, followed by subsequently transferring the developed image to a suitable substrate, and optionally permanently affixing the image thereto.

19. A method of imaging in accordance with claim 18 wherein fixing is accomplished with a fuser roll containing lead oxide and a vinylidene fluoride hexafluoropropylene copolymer.

20. A method of imaging in accordance with claim 18 wherein the photoresponsive device is comprised of a substrate, a photogenerating layer, and a charge transport layer.

21. A method of imaging in accordance with claim 20 wherein the photoregenerating layer is trigonal selenium or vanadyl phthalocyanine, dispersed in a resinous binder, and the charge transport layer is comprised of N,N'-diphenyl-N,N'-bis(3-methylphenyl)1,1'-biphenyl-4,4'-diamine dispersed in a polycarbonate resin.

22. A method of imaging in accordance with claim 18 wherein the resin particles are comprised of a styrene n-butyl methacrylate copolymer, a polyester, or a styrene butadiene copolymer.

23. An improved toner composition in accordance with claim 1 wherein the pigment particles are selected from magenta, cyan, and yellow pigments.

24. An improved toner composition in accordance with claim 1 wherein the pigment particles are selected from magnetites, thereby resulting in the magnetic toner composition.

* * * * *